United States Patent [19]

Kaneyasu et al.

[11] Patent Number: 5,413,691
[45] Date of Patent: May 9, 1995

[54] SOLID ELECTROLYTE GAS-SENSING DEVICE

[75] Inventors: Kazunari Kaneyasu, Fujisawa; Takashi Nakahara, Minoo, both of Japan

[73] Assignee: Tokuyama Corporation, Yamaguchi, Japan

[21] Appl. No.: 172,325

[22] Filed: Dec. 23, 1993

[30] Foreign Application Priority Data

Dec. 25, 1992 [JP] Japan .................. 4-346946

[51] Int. Cl.$^6$ .................................. G01N 27/26
[52] U.S. Cl. .................. 204/424; 204/426; 204/427
[58] Field of Search ............. 204/421, 424, 425, 426, 204/427, 295

[56] References Cited

U.S. PATENT DOCUMENTS

| | | | |
|---|---|---|---|
| 4,715,944 | 12/1987 | Yamagida et al. | 204/426 |
| 5,124,021 | 6/1992 | Kaneyasu et al. | 204/425 |
| 5,273,628 | 12/1993 | Liu et al. | 204/295 |

FOREIGN PATENT DOCUMENTS

| | | |
|---|---|---|
| 0182921 | 6/1986 | European Pat. Off. . |
| 0468249 | 1/1992 | European Pat. Off. . |
| 0470625 | 2/1992 | European Pat. Off. . |
| 3519435 | 12/1986 | Germany . |

OTHER PUBLICATIONS

Miura et al., "High-Performance Solid-Electrolyte Carbon Dioxide Sensor with a Binary Carbonate Electrode", *Sensors and Actuators B*, vol. 9 (1992), pp. 165–170.

Maruyama et al., "Potentiometric Gas Sensor for Carbon Dioxide Using Solid Electrolytes", *Solid State Ionics*, vol. 23 (1987), pp. 107–112.

*Primary Examiner*—John Niebling
*Assistant Examiner*—Bruce F. Bell
*Attorney, Agent, or Firm*—Wenderoth, Lind & Ponack

[57] ABSTRACT

A solid electrolyte gas-sensing device comprising a solid electrolyte layer (a) and a reference electrode layer (b) and a working electrode layer (c) with the solid electrolyte layer (a) being an intermediate layer therebetween, said working electrode layer (c) having a mixture layer (d) in the interface between said solid electrolyte layer (a) and said working electrode layer (c), the mixture layer (d) being formed from a metal salt which shows dissociation equilibrium with a gas to be measured and an electron-conducting substance, the mixture layer (d) containing 0.5 to 14% by volume of the electron-conducting substance.

7 Claims, 2 Drawing Sheets

SOLID ELECTROLYTE GAS-SENSING DEVICE

BACKGROUND OF THE INVENTION

1. Field of the Invention

The present invention relates to a novel solid electrolyte gas-sensing device. More specifically, it relates to a solid electrolyte gas-sensing device for detecting inorganic gases such as carbon dioxide, nitrogen oxides and sulfur oxides in ambient atmosphere, which exhibits high sensitivity for gases to be measured, shows almost no variability from one device to another concerning the initial sensitivity and the sensitivity with time, and therefore has remarkably high reliability.

2. Description of the Related Art

Inorganic gases such as carbon dioxide, nitrogen oxides and sulfur oxides have been hitherto measured in various fields for utilizing the measurement data for fuel control or environmental measurement. For the measurement of these inorganic gases, there have been employed a variety of analysis methods such as an infrared absorption method, an ultraviolet absorption method and a chemiluminescence emission method, while it has been so far pointed out that these methods have a problem in that the apparatuses used therefor are large-scaled and expensive and require maintenance. On the other hand, a solid electrolyte gas-sensing device using a change in the electromotive force of a solid electrolyte layer has been developed as a small-sized, facile and less expensive gas-sensing device which can be a substitute for the above apparatuses.

In detecting inorganic gases such as carbon dioxide, nitrogen oxides and sulfur oxides by means of the above solid electrolyte gas-sensing device, mobile ion species of the solid electrolyte layer and the ion species generated from a gas to be measured are different in some cases. It is hence proposed to use a structure in which an auxiliary electrode comprising metal salt which shows dissociation equilibrium with a gas to be measured is provided on the working electrode side. For example, a solid electrolyte gas-sensing device is known in which the solid electrolyte layer is formed of $\beta$-$Al_2O_3$ or $Na_{1+x}Zr_2Si_xP_{3-x}O_{12}$ (wherein x is 0 to 3, generally referred to as "NASICON") as a sodium ion conductor and the auxiliary electrode is formed of a salt of the same metal as that which forms mobile ion of the solid electrolyte layer (Solid State Ionics 23 107–112, 1987, North-Holland, Amsterdam).

When the above-constituted gas-sensing device is placed in ambient atmosphere containing a gas to be measured, an electromotive force occurs between the two electrodes according to the following Nernst's equation, $$EMF = C - RT/nF \cdot \ln [G] \quad (1)$$

wherein EMF is an electromotive force of the solid electrolyte gas-sensing device, C is a constant, R is a gas constant, T is a temperature of the gas-sensing device, n is an order of reaction, F is a Faraday's constant and [G] is the concentration of a gas to be measured in ambient atmosphere.

The concentration of a gas to be measured can be determined on the basis of the above electromotive force.

FIG. 4 shows the structure of the above solid electrolyte gas-sensing device, in which a reference electrode layer 7 is formed on one surface of a solid electrolyte layer 9, and the other surface is provided with a working electrode layer laminate-formed of an electrode layer 14 and a metal salt as an auxiliary electrode 13. When a gas to be measured reaches the sensing device, a dissociation equilibrium reaction takes place only in the working electrode layer formed of the metal salt 13 and the electrode 14 to cause a change in metal ion amount. This change in the metal ion amount is measured as a change in the electromotive force between the two electrodes of a battery of the solid electrolyte layer 9 according to the above equation (1) with a voltmeter 6, whereby the sensing device can measure the concentration of a gas to be measured. In FIG. 4, numeral 1 indicates a power source, numeral 2 indicates a heater, numeral 3 indicates an alumina substrate, numeral 4 indicates an adhesive, and numeral 5 indicates a lead wire.

However, the solid electrolyte gas-sensing device provided with the above auxiliary electrode has a problem in that the initial sensitivity and the sensitivity with time greatly vary from one device to another and that it is difficult to control the product quality in industrial production. This problem is particularly serious when the mobile ion of the solid electrolyte layer differs from the metal ion of the metal salt as the auxiliary electrode.

Further, as shown in FIG. 5, there is known a carbon dioxide-sensing device having a structure in which an auxiliary electrode 15 formed of a metal salt that shows dissociation equilibrium with a gas to be measured is formed on a solid electrolyte layer 9 and an electrode layer 16 is further laminated thereon.

Japanese Laid-open Patent Publication No. 195,246/1990 discloses a carbon dioxide gas sensor comprising an ion-conducting ceramic plate formed of a solid electrolyte having two electrode layers, one electrode layer on one surface and the other on the other surface, a gas-sensing portion formed of a metal carbonate which is dispersed in one of the two electrode layers and forms dissociation equilibrium with carbon dioxide gas and two lead wires, one wire bonding to one electrode and the other wire bonding to the other electrode, and a heating portion for heating the above gas-sensing portion to a working temperature. Example of the above Japanese Laid-open Patent Publication discloses a carbon dioxide gas sensor having a cathode layer produced by uniformly coating an NASICON plate surface with a dispersion containing an Au paste as an electrode material and 10 to 50 wt %, based on the Au paste, of sodium carbonate, drying the coating and then sintering.

Japanese Laid-open Patent Publication No. 213,565/1992 discloses a $CO_2$ gas sensor comprising a $CO_2$ detecting portion formed of a solid electrolyte, a $CO_2$-sensitive electrode formed on the solid electrolyte and a $CO_2$-insensitive electrode formed on the solid electrolyte and a self-heating heater, the $CO_2$-sensitive electrode being formed from Au metal and other component and having pores through which a gas can at least diffuse. The above Japanese Laid-open Patent Publication discloses that the $CO_2$-sensitive electrode is formed from an Au paste and 30% by weight or less of a solid electrolyte.

The above-structured solid electrolyte gas-sensing device is still to be improved in sensitivity.

SUMMARY OF THE INVENTION

It is therefore an object of the present invention to provide a solid electrolyte gas-sensing device which can detect a gas with good sensitivity and is almost free from the variability in the initial sensitivity and the sensitivity with time.

It is another object of the present invention to provide a solid electrolyte gas-sensing device which has excellent stability in the initial sensitivity and the sensitivity with time.

Other objects and advantages of the present invention will be apparent from the following description.

According to the present invention, the above objects and advantages of the present invention are achieved by a solid electrolyte gas-sensing device comprising a solid electrolyte layer (a) and a reference electrode layer (b) and a working electrode layer (c) with the solid electrolyte layer (a) being an intermediate layer therebetween, said working electrode layer (c) having a mixture layer (d) in the interface between said solid electrolyte layer (a) and said working electrode layer (c), the mixture layer (d) being formed from a metal salt which shows dissociation equilibrium with a gas to be measured and an electron-conducting substance, the mixture layer (d) containing 0.5 to 14% by volume of the electron-conducting substance.

The present invention will be explained hereinafter with reference to the attached drawings, while the present invention shall not specially limited thereto.

Figure 1:
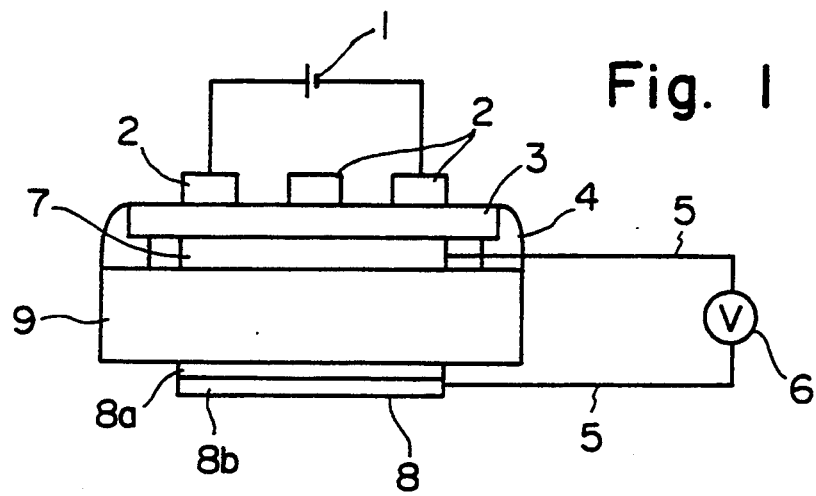
FIG. 1 is a schematic cross-sectional view of a solid electrolyte carbon dioxide-sensing device as a typical embodiment of the present invention.

FIG. 1 shows a typical embodiment of the solid electrolyte gas-sensing device (to be sometimes simply referred to as "gas-sensing device" hereinafter) according to the present invention.

DESCRIPTION OF THE PREFERRED EMBODIMENTS

The solid electrolyte gas-sensing device shown in FIG. 1 has a solid electrolyte layer 9 and a reference electrode 7 and a working electrode 8 with the solid electrolyte layer 9 being an intermediate layer therebetween. The working electrode 8 has a mixture layer 8a in the interface between the above solid electrolyte layer and the working electrode. The mixture layer 8a comprises a metal salt which shows dissociation equilibrium with a gas to be measured and an electron-conducting substance, and the electron-conducting substance is contained in the mixture layer 8a in an amount of 0.5 to 14% by volume.

In the present invention, the solid electrolyte layer 9 can be formed from any solid electrolyte having ion conductivity. Generally, the solid electrolyte is preferably selected from sodium ion conductors such as $Na_{1+x}Zr_2Si_xP_{3-x}O_{12}$ (wherein x is 0 to 3, generally referred to as "NASICON"), $\beta$-$Al_2O_3$ and $\beta$-$Ga_2O_3$, lithium ion conductors such as $Li_{16-2y}Zn_y(GeO_4)_4$ (wherein y is in the range of $0 \leq y < 8$, generally referred to as "LISICON") and $Li_4GeO_4$—$Li_3VO_4$ and oxygen ion conductors such as a mixture of $ZrO_2$ and/or $CeO_2$ with $Y_2O_3$ and/or CaO.

The above solid electrolyte can be obtained by a known production method. Typical examples of the production method include a method in which a raw material powder of any one of the above compound is shaped and then sintered; a method in which the raw material powder is kneaded together with a binder and a solvent to form a paste and a green sheet is formed by a doctor blade method and then sintered; and a method in which any one of the above compounds is laminated on a substrate by a thin film forming method such as a sputtering method.

For achieving the objects of the present invention, the working electrode 8 is required to have a mixture layer of a metal salt, which shows dissociation equilibrium with a gas to be measured, with an electron-conducting substance in the interface between the working electrode 8 and the solid electrolyte layer 9. Further, the electron-conducting substance is required to be contained in the mixture layer in an amount of 0.5 to 14% by volume.

When the solid electrolyte gas-sensing device of the present invention is formed from $Na_2CO_3$ as a metal salt, Au as an electron-conducting substance, NASICON as a solid electrolyte and Au as a reference electrode, battery reactions among the electron-conducting substance Au, the metal salt $Na_2CO_3$, the solid electrolyte and the reference electrode take place among the following substances.

$Na_2CO_3/Au/NASICON/Au$

In the above gas-sensing device, the dissociation equilibrium reaction of the following equation takes place between $Na_2CO_3$ and carbon dioxide in ambient atmosphere.

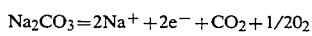

$Na_2CO_3 = 2Na^+ + 2e^- + CO_2 + 1/2O_2$

In the above dissociation equilibrium reaction, not only $Na_2CO_3$ reacts with carbon dioxide in ambient atmosphere, but also $Na_2CO_3$ donates and receives Na ion to and from NASICON as the solid electrolyte, and donates and receives electron to and from Au as the electron-conducting substance. Further, for generating stable electromotive force from the above-structured carbon dioxide-sensing device, NASICON and gold are preferably in contact with each other. That is, the following is presumably required for the solid electrolyte gas-sensing device exhibiting sufficient performance; The solid electrolyte layer, the electron-conducting substance, the metal salt and a gas to be measured should have common interfaces and these interfaces should have a predetermined area or above.

When the amount of the electron-conducting substance based on the metal salt of the mixture layer of the working electrode is less than 0.5% by volume, not only the sensitivity of the gas-sensing device shows a remarkable variability from the initial sensitivity to the sensitivity with time to decrease the yield in industrial production, but also the sensitivity of the gas-sensing device to a gas to be measured is low. When the amount of the electron-conducting substance based on the metal salt exceeds 14% by volume, not only the sensitivity of the gas-sensing device shows a remarkable variability from the initial sensitivity to the sensitivity with time to decrease the yield in industrial production, but also the sensitivity of the gas-sensing device to a gas to be measured is low, and when it exceeds 20% by volume, the gas-sensing device shows almost no sensitivity.

In the present invention, the working electrode 8 is not specially limited so long as it has the above mixture layer 8a in the interface between the working electrode and the solid electrolyte layer 9. For example, the entirety of the working electrode may be formed of the composition of the mixture layer, while the following constitution is preferred for enhancing the electric connection in the gas-sensing device. For enhancing the electrical connection in the sensing device, it is preferable that the mixture layer is present up to a depth of 20 μm or less from the interface to the solid electrolyte layer and the other layer on the mixture layer is formed of more than 14% by volume, preferably 20% by volume or more, of the electron-conducting substance. Further, the concentration of the electron-conducting substance may be continuous or discrete in the interface between the above mixture layer and the other layer.

The method for forming the above working electrode 8 having the mixture layer is not specially limited so long as the electron-conducting substance is contained in an amount of 0.5 to 14% by volume, preferably 2.5 to 9.5% by volume based on the metal salt which shows dissociation equilibrium with a gas to be measured in the interface to the solid electrolyte layer 9. Examples of the method for forming the working electrode preferably include a method in which powders of the electron-conducting substance and the metal salt are mixed in amounts as required and formed into a paste together with a binder such as terpineol and the paste is shaped in a desired form by a screen printing method, a method in which the metal salt is burned at a temperature lower than the decomposition temperature of the metal salt, and a method in which powders of the electron-conducting substance and the metal salt in amounts as required are molded and the molded is shaped in a desired form by a thin film-forming technique such as a sputtering method, an ion plating method or a vapor deposition method. Further, the working electrode 9 may be formed by a method in which the electron-conducting substance is preliminarily uniformly dispersed on the solid electrolyte layer 8 and then a paste of the electron-conducting substance and the metal salt is formed and burned at a temperature lower than the decomposition temperature of the metal salt, or a method in which the metal salt is dispersed as above and then the electron-conducting substance is filled in pores.

There is known a gas-sensing device having a working electrode constituted by forming an electrode layer on a solid electrolyte layer and laminating a metal salt thereon. In producing this gas-sensing device, the working electrode is conventionally formed by a method in which the metal salt is dissolved in a solvent, the electrode layer is impregnated with the solution and the solvent is removed by drying, or a method in which the metal salt is melted on the electrode layer 14. However, when the gas-sensing device is produced by these methods, it is very difficult to overcome the variability in the initial sensitivity and the sensitivity with time. Further, both of the prior art techniques disclosed in Japanese Laid-open Patent Publications Nos. 195246/1990 and 213,565/1989 use more than 14% by volume of an electron-conducting substance, and the sensitivity with time varies to a great extent.

Examples of the electron-conducting substance which constitutes the working electrode 8 and the mixture layer 8a include noble metals such as platinum, gold, silver, palladium and rhodium and oxides of these; perovskite type oxides of the formula $La_{1-z}Sr_zAO_3$ (wherein A is Co, Cu, Fe or Ni and z is a number of from 0.01 to 0.5); and mixtures or composite compounds of the above noble metals or metal oxides with the above perovskite oxides. Preferred are noble metals such as platinum, gold, silver, palladium and rhodium, and more preferred are platinum and gold. The metal salt which constitutes the mixture layer 8a is not specially limited so long as it shows dissociation equilibrium with a gas to be measured. In particular, depending upon gases to be measured such as carbon dioxide, nitrogen oxides and sulfur oxides, the above metal salt is properly selected from carbonates of alkali metals such as Na, Li and K and alkaline earth metals such as Ca, Mg and Ba; carbonates of Bi, Ag, La and Cu; and sulfates and nitrates of alkali metals such as Na, Li and K and alkaline earth metals such as Ca, Mg and Ba. The combination of the metal salt and the material for forming the solid electrolyte layer is not specially limited, while, generally, the effects of the present invention are remarkably exhibited when the mobile ion of the solid electrolyte layer and the metal ion of the metal salt differ from each other.

In the present invention, the reference electrode layer 7 is formed from an electron-conducting substance on the solid electrolyte layer. The reference electrode layer 7 is not specially limited so long as it has a material quality or a structure stable to a gas to be measured. For example, one embodiment is a reference electrode layer which is formed from the above electron-conducting substance alone, and another embodiment is a reference electrode layer formed from a combination of the metal salt which shows dissociation equilibrium with a gas to be measured and the electron-conducting substance, which reference electrode layer is arranged to be in contact with a reference gas.

The gas-sensing device shown in FIG. 1 has an reference electrode layer according to the above former embodiment, in which the reference electrode layer is formed of the electron-conducting substance alone and hence no reference gas is required. This gas-sensing device has a feature in a small and simple structure. The electron-conducting substance for forming the reference electrode is selected from those used for forming the working electrode.

Although not specially limited, the method for producing the above reference electrode is generally selected from a screen printing method, a sputtering method, an ion plating method and a vapor deposition method.

The solid electrolyte gas-sensing device of the present invention is not specially limited in other constitution if it satisfies the above-specified constitution. For example, it may be formed to have the same constitution as that of a known gas-sensing device.

The gas-sensing device of the present invention is used generally by heating it. For heating the gas-sensing device, a heat source outside the device may be employed, or it may be heated as shown in FIG. 1, in which an insulating substrate such as alumina substrate 3 is fixed through an adhesive 4 such as glass, a platinum paste is screen-printed thereon in a wavy form and burned around 1,000° C. to form a heater 2, and a direct current or an alternate current is applied from a power source 1. The site of the heater in the gas-sensing device is not specially limited so long as it does not hamper the operation of the gas-sensing device.

When an organic gas such as toluene, ethyl acetate or ethanol is co-present in an ambient atmosphere to be measured by the gas-sensing device of the present invention, a filter may be used for removing the organic gas.

For example, when the carbon dioxide-sensing device having a heating means, provided by the present invention, is placed within a casing having an aperture for introducing a gas, a filter formed of zeolite may be provided on the aperture or between the aperture and the carbon dioxide-sensing device with some space from the carbon dioxide-sensing device. Since organic gases can be so removed with a filter, the measurement error caused by organic gases which are co-present with carbon dioxide and hamper the measurement of carbon dioxide can be remarkably decreased, and the gas-sensing device of the present invention can continue exhibiting its stable performance for a long period of time.

Zeolite is preferred as the above filter. Zeolite prevents the influence of organic gases on the sensitivity without decreasing the response of the gas-sensing device. Zeolite can be selected from known ones without a special limitation. However, with a decrease in the specific surface area of zeolite, the zeolite tends to show a decreased effect on the removal of organic gases and to decrease the response to carbon dioxide. It is hence preferred to use zeolite having a specific surface area of at least 300 m$^2$/g, preferably at least 500 m$^2$/g, more preferably at least 700 m$^2$/g. Further, the zeolite can be selected from natural and synthetic ones such as A-form zeolite, Z-form zeolite, Y-form zeolite, L-form zeolite, ZSM-5-form zeolite, USY-form zeolite, chabazite, erionite, offretite, mordenite and ferrierite. The above zeolite is not specifically limited concerning an Si/Al ratio and cation.

Of the above zeolites, preferred are Y-form zeolite, mordenite and USY-form zeolite containing Na, NH$_4$ or H as cation and having an Si/Al ratio of 2 to 140, and more preferred are Y-form zeolite containing Na as cation and having an Si/Al ratio of 2 to 5 and USY-zeolite containing Na as cation and having an Si/Al ratio of 4 to 8.

The above zeolite may be used in the form of a powder, or may be used in the form of granulated pellets or beads. As described above, however, zeolite having a specific surface area of at least 300 m$^2$/g is preferred as an organic gas filter, and in view of this point, it is preferred to use a fine powder of zeolite having a particle diameter of 3 μm or less. The powder of zeolite can be generally granulated by kneading the powder together with a binder such as kaolinite, attapulgite, montmorillonite, silica or alumina and a visco-binding additive such as polyvinyl alcohol or ethylene glycol in the presence of water. The pellets are prepared with an extruding pelletizer, while the beads are formed using a rolling granulator.

When the zeolite is used in the form of a powder, the filling density of the zeolite in a retention space is different depending upon the kind of the zeolite, while it is generally 0.01 to 2 g/cm$^3$.

Further, when the gas-sensing device of the present invention is used, the gas concentration can be measured by connecting the two electrodes with a wire 5 through a voltmeter 6 and measuring the electromotive force generated by the contact to a gas to be measured.

In the solid electrolyte gas-sensing device of the present invention, the mixture layer containing specific amounts of the metal salt and the electron-conducting substance is present in the interface between the solid electrolyte layer and the working electrode. As a result, the solid electrolyte layer, the electron-conducting substance, the metal salt and a gas to be measured have common interfaces uniformly and sufficiently. An equilibrium reaction between the gas to be measured and the metal salt are therefore considered to take place rapidly and uniformly. It is also considered that the metal salt is required to be present in an excess amount relative to the electron-conducting substance, since the metal salt which plays a central role in the dissociation equilibrium reaction with a gas to be measured contributes the most among the substances which form the above common interfaces.

The solid electrolyte gas-sensing device of the present invention has features in that the sensitivity to a gas to be measured is high, that the variability from one device to another in industrial production is small concerning the initial sensitivity and the sensitivity with time and that it has excellent stability.

Therefore, the solid electrolyte gas-sensing device of the present invention shows a high yield in industrial production, and it is highly industrially significant.

Further, the above effects are remarkable particularly in the case where in the solid electrolyte gas-sensing device, the mobile ion of the solid electrolyte layer differs from the metal ion of the metal salt.

The present invention will be explained more in detail hereinafter with reference to Examples. However, the present invention shall not be limited to these Examples.

EXAMPLES 1–5 AND COMPARATIVE EXAMPLES 1–3

A solid electrolyte gas-sensing device for measuring carbon dioxide (simply referred to "gas-sensing device" hereinafter), shown in FIG. 1, was produced as follows.

A powder of NASICON was shaped and sintered to form a disk-like sintered body having a diameter of about 5 mm and a thickness of about 0.7 mm, which was used as a solid electrolyte layer 9. A gold paste was screen-printed on one surface of the solid electrolyte layer 9, dried and then baked at 700° C. to form a reference electrode 7.

A plurality of solid electrolyte layers 9 with reference electrodes 7 formed on one surfaces were prepared in the same manner as above.

A working electrode 8 was formed on the other surface of the solid electrolyte layer 9 as follows. That is, a uniform mixture containing a lithium carbonate powder and a gold powder in amounts (unit: % by volume) shown in Table 1 was formed into a paste using a vehicle prepared by dissolving 5% by weight of ethyl cellulose in terpineol, and the paste was screen-printed on the other surface of the above solid electrolyte layer 9, dried and baked at 650° C. to form a mixture layer 8a having a thickness of about 8 μm, which was to constitute a working electrode 8.

A gold paste (trade name: 8835, supplied by ESL) was screen-printed on the mixture layer 8a, dried and baked at 650° C. to form a layer 8b composed substantially of gold, whereby the working electrode 8 was formed.

Separately, a platinum paste was screen-printed on an alumina substrate 3 and baked to form a heater 2 having a wavy form, and the alumina substrate 3 was bonded to the reference electrode 7 through an adhesive 4 formed of glass.

Eight gas-sensing devices having mixture layers 8a whose gold contents differed were prepared as above, and used while heating them at 450° C. by applying direct current to their heaters 2 from a power source 1.

The above gas-sensing devices were evaluated for their sensitivity to carbon dioxide as follows. The gas-sensing devices were allowed to stand in an ambient atmosphere having a carbon dioxide concentration of 350 ppm nearly equivalent to the carbon dioxide concentration in the atmosphere, and while the carbon dioxide concentration in the ambient atmosphere was changed up to 30,350 ppm, the gas-sensing devices were measured for their electromotive forces with a voltmeter 6.

Table 1 shows the sensitivity of each device, which was calculated by deducting a value of the electromotive force in the measured ambient atmosphere from a value of the electromotive force in the ambient atmosphere containing 350 ppm of carbon dioxide.

The above Examples of the present invention show that the sensitivity is in proportion to the logarithm of the carbon dioxide concentration. Therefore, a calibration curve is prepared on the basis of this relationship and arranged to correspond to the values of the electromotive force of the gas-sensing device, whereby the carbon dioxide concentration to be measured in an atmosphere can be determined.

TABLE 1

| Lithium carbonate vol. % | Gold vol. % | Sensitivity to carbon dioxide gas (mV) Carbon dioxide concentration (ppm) | | | | |
| --- | --- | --- | --- | --- | --- | --- |
| | | 650 | 1,350 | 3,350 | 10,350 | 30,350 |
| CEx. 1 | 50.4 | 49.6 | 2 | 4 | 5 | 12 | 38 |
| CEx. 2 | 83.1 | 16.9 | 11 | 25 | 41 | 62 | 80 |
| Ex. 1 | 88.4 | 11.6 | 15 | 31 | 51 | 78 | 103 |
| Ex. 2 | 93.2 | 6.8 | 15 | 32 | 56 | 86 | 115 |
| Ex. 3 | 97.3 | 2.7 | 14 | 25 | 49 | 79 | 107 |
| Ex. 4 | 97.9 | 2.1 | 11 | 25 | 42 | 62 | 81 |
| Ex. 5 | 99.1 | 0.9 | 11 | 25 | 43 | 63 | 82 |

TABLE 1-continued

| Lithium carbonate vol. % | Gold vol. % | Sensitivity to carbon dioxide gas (mV) Carbon dioxide concentration (ppm) | | | | |
| --- | --- | --- | --- | --- | --- | --- |
| | | 650 | 1,350 | 3,350 | 10,350 | 30,350 |
| CEx. 3 | 99.9 | 0.1 | 10 | 22 | 38 | 57 | 75 |

CEx. = Comparative Example,
Ex. = Example

For evaluating the above gas-sensing devices for the variability of the initial sensitivity and the sensitivity with time and a decrease in the sensitivity with time, a plurality of gas-sensing devices were produced according to each Example or Comparative Example, and five devices were arbitrarily taken out per Example or Comparative Example. These gas-sensing devices were measured for an average sensitivity and a standard deviation in an ambient atmosphere having a carbon dioxide concentration of 3,000 ppm per Example or Comparative Example. Table 2 shows the results.

TABLE 2

| | At initial stage | | After 50 days | | After 100 days | | After 150 days | |
| --- | --- | --- | --- | --- | --- | --- | --- | --- |
| | Average gas sensitivity (mv) | Standard deviation | Average gas sensitivity (mv) | Standard deviation | Average gas sensitivity (mv) | Standard deviation | Average gas sensitivity (mv) | Standard deviation |
| CEx. 1 | 4.7 | 0.67 | 4.3 | 0.56 | 3.6 | 0.60 | 2.4 | 0.50 |
| CEx. 2 | 40.0 | 0.48 | 34.0 | 4.86 | 25.2 | 11.5 | 17.4 | 12.8 |
| Ex. 1 | 51.3 | 0.72 | 51.0 | 0.74 | 51.1 | 0.73 | 50.9 | 0.77 |
| Ex. 2 | 50.2 | 0.77 | 50.2 | 0.78 | 50.1 | 0.80 | 50.2 | 0.81 |
| Ex. 3 | 49.8 | 0.82 | 48.2 | 0.75 | 48.6 | 0.80 | 48.2 | 1.47 |
| Ex. 4 | 42.3 | 1.33 | 41.5 | 1.20 | 41.3 | 1.17 | 40.7 | 1.17 |
| Ex. 5 | 43.0 | 0.63 | 42.6 | 0.80 | 42.3 | 0.75 | 41.6 | 1.18 |
| CEx. 3 | 37.2 | 1.72 | 33.2 | 2.93 | 29.4 | 4.84 | 24.5 | 8.66 |

CEx. = Comparative Example,
Ex. = Example

Comparative Examples 1 and 2 show cases where the volume ratio of gold is greater than that in the range of the present invention. These cases clearly show that with an increase in the volume ratio of gold, the sensitivity deceases to a great extent, that the initial sensitivity and the sensitivity with time greatly vary, and that the sensitivity greatly decreases with time.

On the other hand, Comparative Example 3 shows a case where the volume ratio of gold is smaller than that in the range of the present invention. It is seen in this case that the sensitivity decreases and the output of the electromotive force becomes unstable. In this case, further, it is seen that the initial sensitivity and the sensitivity with time greatly vary and the sensitivity greatly decreases with time.

EXAMPLES 6 AND 7 AND COMPARATIVE EXAMPLES 4 AND 5

Solid electrolyte gas-sensing devices in the same manner as in Example 1 except that the mixture layers 8a which were to constitute working electrodes 8 were formed on the solid electrolyte layers with reference electrodes as follows.

That is, a uniform mixture containing a barium nitrate powder and a gold powder in amounts (unit: % by volume) shown in Table 3 was formed into a paste using a vehicle prepared by dissolving 5% by weight of ethyl cellulose in terpineol, and the paste was screen-printed on the surface of each of the above solid electrolyte layers 9, dried and sintered at 600° C. to form mixture layers 8a having a thickness of about 12 μm, which were to constitute working electrodes 8.

Eight gas-sensing devices having mixture layers 8a whose gold contents differed were prepared as above, and used while heating them at 450° C. by applying direct current to their heaters 2 from a power source 1.

The above gas-sensing devices were evaluated for their sensitivity to nitrogen dioxide as follows. The gas-sensing devices were allowed to stand in atmosphere, and while the nitrogen dioxide concentration in the atmosphere was changed to 200 ppm, the gas-sensing devices were measured for their electromotive forces with a voltmeter 6.

Table 3 shows the sensitivity of each device, which was calculated by deducting a value of the electromotive force in the measured ambient atmosphere from a value of the electromotive force in atmosphere.

The above Examples of the present invention show that the sensitivity is in proportion to the logarithm of the nitrogen dioxide concentration. Therefore, a calibration curve is prepared on the basis of this relationship and arranged to correspond to the values of the electromotive force of the gas-sensing device, whereby the nitrogen dioxide concentration to be measured in an atmosphere can be determined.

TABLE 3

| | Barium nitrate (vol. %) | Gold (vol. %) | Sensitivity to nitrogen dioxide gas (mV) Nitrogen dioxide concentration (ppm) | | | |
|---|---|---|---|---|---|---|
| | | | 10 | 50 | 100 | 200 |
| Ex. 6 | 93.5 | 6.5 | 99 | 126 | 138 | 149 |
| Ex. 7 | 97.0 | 3.0 | 92 | 116 | 126 | 137 |
| CEx. 4 | 50.0 | 50.0 | 26 | 32 | 35 | 37 |
| CEx. 5 | 99.9 | 0.1 | 55 | 71 | 78 | 84 |

For evaluating the above gas-sensing devices for the variability of the initial sensitivity and the sensitivity with time and a decrease in the sensitivity with time, a plurality of gas-sensing devices were produced according to each Example, and five devices were arbitrarily taken out per Example or Comparative Example. These gas-sensing devices were measured for an average sensitivity and a standard deviation in an ambient atmosphere having a nitrogen dioxide concentration of 100 ppm per Example or Comparative Example. Table 4 shows the results.

TABLE 4

| | At initial stage | | After 50 days | | After 100 days | | After 150 days | |
|---|---|---|---|---|---|---|---|---|
| | Average gas sensitivity (mv) | Standard deviation | Average gas sensitivity (mv) | Standard deviation | Average gas sensitivity (mv) | Standard deviation | Average gas sensitivity (mv) | Standard deviation |
| Ex. 6 | 137.8 | 1.33 | 137.2 | 1.88 | 136.0 | 2.45 | 135.3 | 2.47 |
| Ex. 7 | 125.6 | 1.36 | 125.0 | 1.10 | 124.5 | 1.36 | 123.6 | 1.36 |
| CEx. 4 | 34.0 | 36.8 | 22.0 | 24.4 | 10.2 | 10.4 | 4.6 | 2.94 |
| CEx. 5 | 76.6 | 10.7 | 66.3 | 13.9 | 61.0 | 15.6 | 55.4 | 16.7 |

CEx. = Comparative Example.
Ex. = Example

Comparative Example 4 show a case where the volume ratio of gold is greater than that in the range of the present invention. This case clearly shows that with an increase in the volume ratio of gold, the sensitivity deceases to a great extent, that the initial sensitivity and the sensitivity with time greatly vary, and that the sensitivity greatly decreases with time.

On the other hand, Comparative Example 3 shows a case where the volume ratio of gold is smaller than that in the range of the present invention. It is seen in this case that the sensitivity decreases and the output of the electromotive force becomes unstable. In this case, further, it is seen that the initial sensitivity and the sensitivity with time greatly vary and the sensitivity greatly decreases with time.

EXAMPLES 8 AND 9

Solid electrolyte gas-sensing devices were produced in the same manner as in Example 1 except for the following (1) and (2).

(1) A powder of $\beta$-A1203 was shaped and sintered to form a solid electrolyte layer 9.

(2) A uniform mixture of a carbonate shown in Table 5 with gold in an amount of 9% by volume based on the carbonate was formed into a paste using a vehicle prepared by dissolving 5% by weight of ethyl cellulose in terpineol, and the paste was screen-printed, air-dried and sintered at 800° C. to form a mixture layer 8a.

The above-obtained gas-sensing devices were evaluated for their sensitivity to carbon dioxide as follows. The gas-sensing devices were allowed to stand in an ambient atmosphere having a carbon dioxide concentration of 350 ppm nearly equivalent to the carbon dioxide concentration in the atmosphere, and while the carbon dioxide concentration in the ambient atmosphere was changed up to 30,350 ppm, the gas-sensing devices were measured for their electromotive forces with a voltmeter 6.

Table 5 shows the sensitivity of each device, which was calculated by deducting a value of the electromotive force in the measured ambient atmosphere from a value of the electromotive force in the ambient atmosphere containing 350 ppm of carbon dioxide.

The above Examples of the present invention show that the sensitivity is in proportion to the logarithm of the carbon dioxide concentration. Therefore, a calibration curve is prepared on the basis of this relationship and arranged to correspond to the values of the electromotive force of the gas-sensing device, whereby the carbon dioxide concentration to be measured in an atmosphere can be determined.

TABLE 5

| | Sensitivity to carbon dioxide gas (mV) Carbon dioxide concentration (ppm) | | | | |
|---|---|---|---|---|---|
| Carbonate | 650 | 1,350 | 3,350 | 10,350 | 30,350 |
| Ex. 8 BaCO$_3$ | 15 | 33 | 57 | 80 | 108 |
| Ex. 9 K$_2$CO$_3$ | 14 | 31 | 53 | 78 | 105 |

Ex. = Example

For evaluating the above gas-sensing devices for the variability of the initial sensitivity and the sensitivity with time and a decrease in the sensitivity with time, a plurality of gas-sensing devices were produced according to each Example, and five devices were arbitrarily taken out per Example. These gas-sensing devices were measured for an average sensitivity and a standard deviation in an ambient atmosphere having a carbon dioxide concentration of 3,000 ppm. Table 6 shows the results.

TABLE 6

|  | At initial stage | | After 50 days | | After 100 days | | After 150 days | |
| --- | --- | --- | --- | --- | --- | --- | --- | --- |
|  | Average gas sensitivity (mv) | Standard deviation | Average gas sensitivity (mv) | Standard deviation | Average gas sensitivity (mv) | Standard deviation | Average gas sensitivity (mv) | Standard deviation |
| Ex. 8 | 55.2 | 1.33 | 54.8 | 0.98 | 54.4 | 1.02 | 54.0 | 0.89 |
| Ex. 9 | 53.4 | 1.02 | 52.8 | 1.11 | 52.8 | 1.04 | 52.5 | 1.20 |

Ex. = Example

EXAMPLE 10

Figure 2:
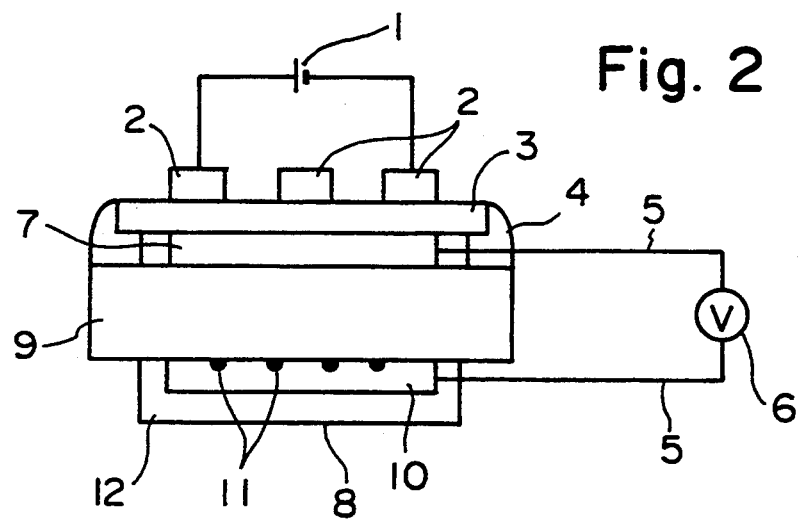
FIG. 2 is a schematic cross-sectional view of a solid electrolyte carbon dioxide-sensing device as another typical embodiment of the present invention.

A solid electrolyte carbon dioxide-sensing device having the structure shown in FIG. 2 was produced as follows.

A solid electrolyte layer 9 was formed in the same manner as in Example 1, and a gold paste was screen-printed on one surface of the solid electrolyte layer 9, dried and baked at 700° C. to form a reference electrode layer 7. A fine powder 11 of gold was dispersed in terpineol and the resultant dispersion was applied to the other surface of the solid electrolyte layer 9 and dried. Lithium carbonate as a metal salt was formed into a paste using a vehicle prepared by dissolving 5% by weight of ethyl cellulose in terpineol, and the paste was screen-printed on the dried fine powder 11 of gold, dried and calcined at 650° C. In the above procedures, a mixture layer 10 was adjusted such that the area of gold in the interface to the solid electrolyte layer was 8.5% by volume based on the lithium carbonate. An electrode 12 was formed on the mixture layer in the same manner as in the formation of the above reference electrode layer 7 except that the calcining temperature was changed to 650° C. for improving the electric contact. A heater was bonded to the reference electrode layer 7 in the same manner as in Example 1. The so-obtained gas-sensing device was used while heating it at 450° C. by applying direct current to the heater 2 from a power source 1.

The gas-sensing device was also evaluated for the sensitivity to carbon dioxide in the same manner as in Example 1.

Table 7 shows the sensitivity to carbon dioxide gas. The sensitivity of the gas-sensing device increased with an increase in the carbon dioxide concentration, and the values thereof were very large. The relationship between the carbon dioxide concentration and the sensitivity was the same as that in Example 1, and it was shown that the sensitivity was in proportion to the logarithm of the carbon dioxide concentration. As a result, the concentration of carbon dioxide in ambient atmosphere can be determined by measuring the electromotive force of the gas-sensing device.

TABLE 7

|  |  | Sensitivity to carbon dioxide gas (mV) Carbon dioxide concentration (ppm) | | | | |
| --- | --- | --- | --- | --- | --- | --- |
|  | Carbonate | 650 | 1,350 | 3,350 | 10,350 | 30,350 |
| Ex. 10 | $Li_2CO_3$ | 13 | 30 | 51 | 76 | 101 |

Ex. = Example

For evaluating the above gas-sensing device for the variability of the initial sensitivity and the sensitivity with time and a decrease in the sensitivity with time, a plurality of gas-sensing devices were produced in the same manner as above, and five devices were arbitrarily taken out and measured for an average sensitivity and a standard deviation in an ambient atmosphere having a carbon dioxide concentration of 3,000 ppm. Table 8 shows the results.

TABLE 8

|  | At initial stage | | After 50 days | | After 100 days | | After 150 days | |
| --- | --- | --- | --- | --- | --- | --- | --- | --- |
|  | Average gas sensitivity (mv) | Standard deviation | Average gas sensitivity (mv) | Standard deviation | Average gas sensitivity (mv) | Standard deviation | Average gas sensitivity (mv) | Standard deviation |
| Ex. 10 | 50.0 | 0.63 | 49.6 | 0.49 | 49.4 | 0.49 | 49.1 | 0.75 |

Ex. = Example

EXAMPLES 11–22 AND COMPARATIVE EXAMPLES 6 AND 7

Figure 3:
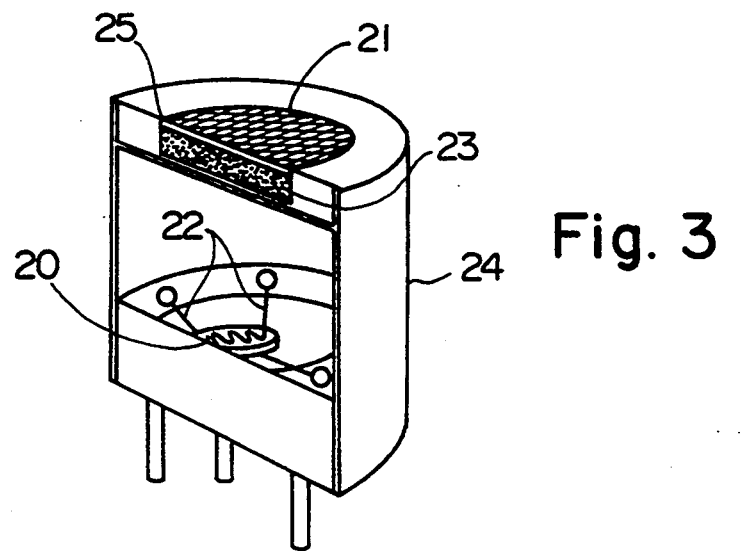
FIG. 3 is a schematic perspective view of a carbon dioxide sensor with a gas-sensing device and an organic gas filter, provided by the present invention, in which the carbon dioxide sensor is cut along its vertical central plane.
Figure 4:
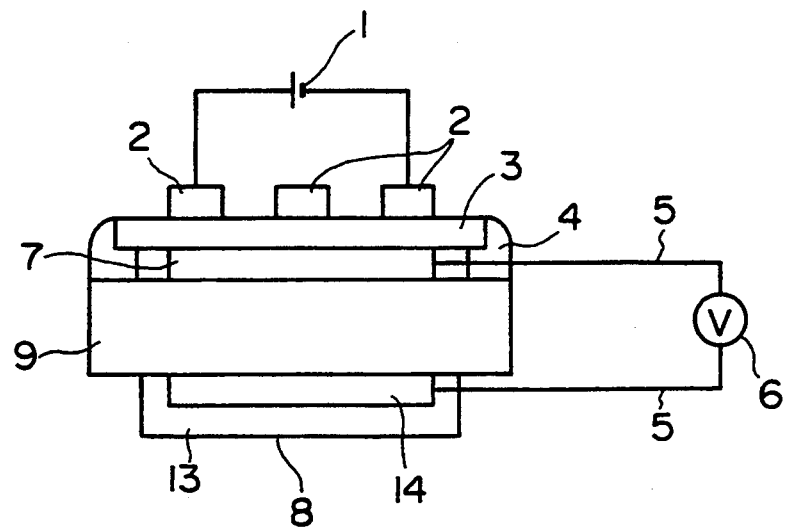
FIG. 4 is s schematic cross-sectional view of a conventional solid selectrolyte carbon dioxide-sensing device.
Figure 5:
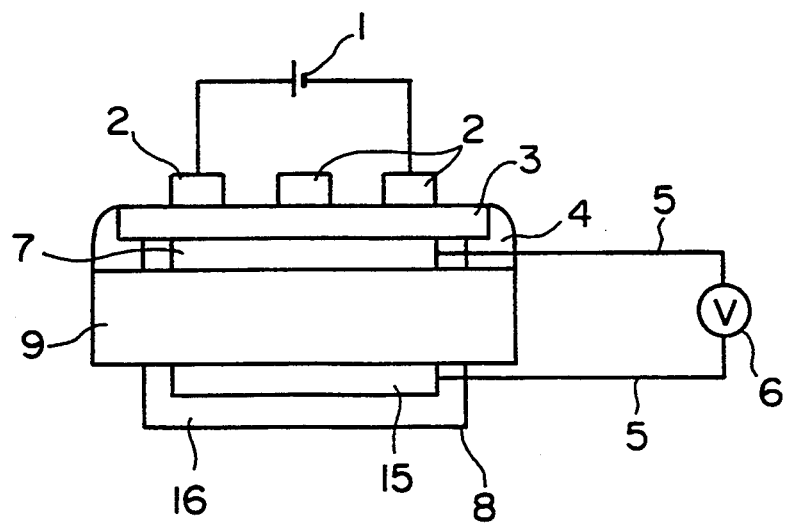
FIG. 5 is a schematic cross-sectional view of another conventional solid electrolyte carbon dioxide-sensing device.

The same gas-sensing device 20 as that obtained in Example 1 was used to produce a $CO_2$ gas sensor having the structure shown in FIG. 3.

That is, lead wires 22 of platinum bonded to the gas-sensing device 20 were spot-welded to electrically conductive pins provided in the bottom of a casing 24 shown in FIG. 3. A filter 23 was constituted by filling a zeolite shown in Table 9 into a filling space which was formed of a mesh plate 21 and had a thickness of 4.0 mm. Numeral 25 indicates apertures.

The above filter was placed with a space from the carbon dioxide-sensing device being provided such that it had a temperature of 30°, 60°, 100° or 130° C. under heat by the heater 6 of the device.

TABLE 9

|  | Organic gas filter | | | | |
| --- | --- | --- | --- | --- | --- |
|  | Zeolite | | | | |
|  | Name | Cation | Si/Al | Specific area (m²/g) | Temp. (°C.) |
| Ex. 11 | Y form | Na | 2.4 | 565 | 60 |
| Ex. 12 | USY form | Na | 5.9 | 598 | 60 |
| Ex. 13 | Y form | H | 5.9 | 700 | 60 |
| Ex. 14 | USY form | Na | 139.8 | 1,158 | 60 |
| Ex. 15 | Y form | H | 2.4 | 655 | 60 |
| Ex. 16 | mordenite | Na | 5.0 | 330 | 60 |
| Ex. 17 | Y form | $NH_4$ | 5.9 | 647 | 60 |
| Ex. 18 | mordenite | Na | 10.5 | 425 | 60 |
| Ex. 19 | USY form | Na | 14.1 | 787 | 60 |
| Ex. 20 | USY form | Na | 139.8 | 1,158 | 130 |
| Ex. 21 | USY form | Na | 139.8 | 1,158 | 100 |
| Ex. 22 | USY form | Na | 139.8 | 1,158 | 30 |
| CEx. 6 | activated carbon | | | | 60 |

TABLE 9-continued

| | Organic gas filter | | | |
|---|---|---|---|---|
| | Zeolite | | | |
| Name | Cation | Si/Al | Specific area (m²/g) | Temp. (°C.) |
| CEx. 7 | not filled | | | 60 |

Ex. = Example.
CEx. = Comparative Example

For evaluating the above-constituted carbon dioxide sensor for the influence by organic gases, the sensor was placed in an ambient atmosphere having a carbon dioxide concentration of 2% or in an ambient atmosphere containing a combination of 350 ppm of carbon dioxide with 1,000 ppm of toluene, ethyl acetate or ethanol as an organic gas, and measured for sensitivity.

Further, the above carbon dioxide sensor was evaluated for its response as a response time when the carbon dioxide concentration was changed from 350 ppm to 3,000 ppm. That is, the response time is a length of time from a time when the ambient atmosphere is changed to a time when the electromotive force reaches 90% of that in the ambient atmosphere having a carbon dioxide concentration of 3,000 ppm. Table 10 shows the results.

Further, a carbon dioxide sensor using activated carbon in place of the zeolite and a carbon dioxide sensor using no zeolite were measured for their gas sensitivity in the same manner as above. Table 10 shows the results.

TABLE 10

| | Sensitivity to carbon dioxide (mV) | Sensitivity to toluene* (mV) | Sensitivity to ethyl acetate* (mV) | Sensitivity to ethanol* (mV) | Response time (sec.) |
|---|---|---|---|---|---|
| Ex. 11 | 102.2 | 8.7 | 2.3 | 5.8 | 58 |
| Ex. 12 | 103.1 | 9.3 | 6.5 | 7.2 | 35 |
| Ex. 13 | 102.5 | 8.5 | 5.8 | 9.8 | 31 |
| Ex. 14 | 101.8 | 9.0 | 6.0 | 10.3 | 23 |
| Ex. 15 | 102.0 | 9.4 | 11.3 | 14.8 | 45 |
| Ex. 16 | 101.7 | 10.2 | 13.6 | 15.2 | 68 |
| Ex. 17 | 102.9 | 12.8 | 9.7 | 12.0 | 54 |
| Ex. 18 | 101.9 | 9.2 | 4.5 | 6.8 | 69 |
| Ex. 19 | 103.0 | 4.5 | 1.9 | 13.7 | 25 |
| Ex. 20 | 102.5 | 2.8 | 5.7 | 9.9 | 24 |
| Ex. 21 | 102.7 | 4.2 | 3.0 | 9.5 | 25 |
| Ex. 22 | 101.9 | 10.1 | 7.8 | 14.7 | 31 |
| CEx. 6 | 102.5 | 19.3 | 18.2 | 16.3 | 142 |
| CEx. 7 | 101.8 | 87.6 | 103.5 | 75.6 | 27 |

CEx. = Comparative Example,
Ex. = Example
Note:
*Ambient atmosphere contained 350 ppm of carbon dioxide in combination with this organic gas.

The sensitivity to carbon dioxide when zeolite is used as the organic gas filter as shown in Examples 11 to 22 and when activated carbon is used as shown in Comparative Example 6 is almost the same as that when no filtering substance is used as shown in Comparative Example 2. It is hence shown that the filter has no influence on the response of the gas-sensing device to carbon dioxide. On the other hand, the sensitivity to organic gases when activated carbon is used as the organic gas filer as shown in Comparative Example 6 is decreased approximately to ¼ to 1/5 of that when no filtering substance is used as shown in Comparative Example 7. In contrast, the sensitivity when zeolite is used is much smaller than that when activated carbon is used as shown in Comparative Example 6. In particular, when zeolites as shown in Examples 11 to 14, 18, 19 and 20 to 22 are used, the effect on the removal of organic gases is high and the results are excellent. Further, zeolite tends to show a higher effect on the removal of toluene and ethyl acetate.

The response when activated carbon is filled as shown in Comparative Example 6 is extremely poor since the response time in this case is at least four times as long as that when no filtering substance is filled as shown in Comparative Example 7. In contrast, the response when zeolite having a specific surface area of approximately 300 to 650 m²/g is used as shown in Examples 11, 12 and 15 to 18 is slower than that when no filtering substance is used as shown in Comparative Example 7, while the response time in these Examples 11, 12 and 15 to 18 is about ½ of that when activated carbon is used. Further, when zeolite having a specific surface area of 700 m²/g or more is used as shown in Examples 13, 14 and 19 to 22, only the sensitivity to ethanol can be fully decreased without impairing the response.

What is claimed is:

1. A solid electrolyte gas-sensing device comprising a solid electrolyte layer (a) and a reference electrode layer (b) and a working electrode layer (c) with the solid electrolyte layer (a) being an intermediate layer therebetween, said working electrode layer (c) having a mixture layer (d) in the interface between said solid electrolyte layer (a) and said working electrode layer (c), the mixture layer (d) being formed from a metal salt which shows dissociation equilibrium with a gas to be measured and an electron-conducting substance, the mixture layer (d) containing 0.5 to 14% by volume of the electron-conducting substance.

2. The device of claim 1, wherein the solid electrolyte layer (a) has conductivity for sodium ion, lithium ion or oxygen ion.

3. The device of claim 1, wherein the solid electrolyte layer (a) is selected from the group consisting of $Na_{1+x}Zr_2Si_xP_{3-x}O_{12}$ wherein x is 0 to 3, $\beta$-$Al_2O_3$, $\beta$-$Ga_2O_3$, $Li_{16-2y}Zn_y(GeO_4)_4$ wherein y is in the range of $0 \leq y < 8$, $Li_4GeO_4$—$Li_3VO_4$ and a mixture of $ZrO_2$ and/or $CeO_2$ with $Y_2O_3$ and/or $CaO$.

4. The device of claim 1, wherein the electron-conducting substance forming the mixture layer (d) is selected from the group consisting of platinum, gold, silver, palladium, rhodium, oxides of these, $La_{1-z}Sr_zAO_3$ wherein A is Co, Cu, Fe or Ni and z is a number of from 0.01 to 0.5, and mixtures of these.

5. The device of claim 1, wherein the metal salt forming the mixture layer (d) is selected from the group consisting of alkali metal carbonates, alkali metal sulfates, alkali metal nitrates, alkaline earth metal carbonates, alkaline earth metal sulfates, alkaline earth metal nitrates, Bi carbonate, Ag carbonate, La carbonate and Cu carbonate.

6. The device of claim 1, wherein the mixture layer (d) is present up to a depth of 20 μm or less from an interface to the solid electrolyte layer, and a mixture layer, other than the mixture layer (d), containing more than 14% by volume of an electron-conducting substance and a metal salt is present on that surface of the mixture layer (d) which is opposite to the interface.

7. A solid electrolyte gas sensor provided with the device of claim 1 and a filter formed of zeolite.

* * * * *